United States Patent [19]
Hynynen et al.

[11] Patent Number: 6,074,352
[45] Date of Patent: Jun. 13, 2000

[54] METHOD FOR THE TREATMENT OF JOINT DISEASES CHARACTERIZED BY UNWANTED PANNUS

[75] Inventors: Kullervo Hynynen, Medfield, Mass.; Karoly Foldes, Budapest, Hungary; Ferenc A. Jolesz, Brookline, Mass.; Carl Winalski, Westwood, Mass.; Sonya Shortkroff, Braintree, Mass.

[73] Assignee: Brigham and Women's Hospital, Boston, Mass.

[21] Appl. No.: 09/048,866

[22] Filed: Mar. 26, 1998

[51] Int. Cl.⁷ .................................................. A61B 17/00
[52] U.S. Cl. .............................. 601/3; 600/411; 600/427; 600/439
[58] Field of Search ................................ 600/411, 427, 600/439; 601/2–4; 604/20, 22

[56] References Cited

U.S. PATENT DOCUMENTS

| | | |
|---|---|---|
| 3,867,929 | 2/1975 | Joyner et al. . |
| 4,185,502 | 1/1980 | Frank . |
| 4,620,546 | 11/1986 | Aida et al. ............................... 128/660 |
| 4,758,429 | 7/1988 | Gordon ...................................... 424/85 |
| 5,080,102 | 1/1992 | Dory ....................................... 128/660 |
| 5,149,319 | 9/1992 | Unger . |
| 5,172,692 | 12/1992 | Kulow et al. . |
| 5,275,165 | 1/1994 | Ettinger et al. . |
| 5,368,032 | 11/1994 | Clline et al. . |
| 5,380,411 | 1/1995 | Schlief .............................. 204/157.15 |
| 5,413,550 | 5/1995 | Castel . |
| 5,514,130 | 5/1996 | Baker ....................................... 606/41 |
| 5,549,544 | 8/1996 | Young et al. . |
| 5,810,888 | 9/1998 | Fenn . |
| 5,811,447 | 9/1998 | Kunz et al. . |

*Primary Examiner*—Marvin M. Lateef
*Assistant Examiner*—Shawna J. Shaw
*Attorney, Agent, or Firm*—Lahive & Cockfield, LLP; Giulio A. Conti, Jr., Esq.

[57] ABSTRACT

The present invention describes methods for the treatment of joint diseases characterized by unwanted pannus, e.g., arthritis. The method involves the introduction of ultrasound energy into the inflamed cells or pannus of the joint to be treated resulting in destruction and/or modification of the pannus.

12 Claims, 3 Drawing Sheets

METHOD FOR THE TREATMENT OF JOINT DISEASES CHARACTERIZED BY UNWANTED PANNUS

RELATED APPLICATION

This application is related to U.S. application Ser. No. 09/048,864 entitled "Transmyocardial Revascularization Using Ultrasound," with attorney docket no: BWI-134 filed Mar. 26, 1998, the teachings of which are incorporated herein by reference.

BACKGROUND OF THE INVENTION

Hyperplastic synovial joint diseases, such as rheumatoid arthritis, are disorders that can cause a condition known as synovial hyperplasia synovitis. Examples of such joint diseases include, e.g., inflammatory arthritides, including infection, deposition diseases such as amyloid arthropathy, as well as other disorders such as, neoplastic-like diseases such as pigmented villonodular synovitis. Synovial hyperplasia is an overgrowth of the inner layer of an articular capsule surrounding a joint. This inner layer is otherwise known as the synovial membrane. The synovial hyperplasia can further result in progressive destruction, deformity, and/or disability of the joint. The hyperplastic synovial membrane includes proliferation of the synovial cells and in many cases, inflammatory cells or proteins that may collect in the synovial membrane of the joint. The hyperplastic synovial membrane can be referred to as "pannus". Destruction or modification of the pannus can prevent joint destruction, deformity, and/or disability within the joint.

SUMMARY OF THE INVENTION

Methods of the invention are based in part on the discovery of a novel method for preventing the deterioration and/or destruction of joints which are afflicted with unwanted pannus, e.g., arthritis or other hyperplastic synovial joint diseases. Through the introduction of ultrasound energy into the joint to be treated, the pannus can be destroyed or modified to reduce the inflammatory response and prevent or decrease the amount of joint deterioration and/or destruction.

Accordingly, in one aspect, the invention provides a method of treating hyperplastic synovial joint diseases, e.g., arthritis. The method includes the steps of focusing a beam of ultrasound energy on the pannus so that the pannus is destroyed or modified.

In another aspect, the invention provides a method for the treatment of arthritis and other hyperplastic synovial joint diseases, comprising the steps of focusing a beam of ultrasound energy on the pannus so that the internal temperature of the pannus at a level sufficient to coagulate the plannus.

In still another aspect, the invention provides a method for the treatment of arthritis and other hyperplastic synovial joint diseases, comprising the steps of focusing a beam of ultrasound energy on the pannus so that the cavitation effects of the ultrasound energy destroys or modifies the pannus.

In yet another aspect, the invention provides a method for the treatment of arthritis and other inflammatory joint diseases, comprising the steps of focusing multiple short and high powered beams of ultrasound energy so that the pannus is vaporized.

In still yet another aspect, the invention provides a method for the treatment of arthritis and other inflammatory joint diseases, comprising the steps of utilizing a multiphase array to focus a beam of ultrasound energy on the pannus so that the pannus is destroyed or modified.

In an additional aspect, the previously described methods utilize a lens to focus the beam of ultrasound energy. In yet another additional aspect, the previously described methods utilize magnetic resonance imaging (MRI) an image guidance system.

In still another additional aspect, the previously described methods control the MRI guidance system with a central processing unit for precise guidance. In still yet another additional aspect, the previously described methods do not damage the surrounding normal tissue or bone.

According to one aspect of the invention, the novel system may deliver ultrasonic energy in the range of about 0.2 to about 50 MHz. More particularly, a range of about 0.5 to about 20 MHz is preferred and still more preferable is a range of even about 1.0 to about 10 MHz.

According to another aspect of the invention, the ultrasonic energy is delivered in multiple treatments more than two minutes, one hour, or one day apart.

Conventional methods for destroying or modifying pannus have included open surgery and radiation therapy. The present invention provides an alternative to treating arthritis and other inflammatory diseases and uses noninvasive ultrasound energy to destroy or modify the pannus. Methods, as described herein, can replace invasive surgery and radiation therapy which are often used as a last resort for treatment. This novel therapy is noninvasive and controlled. Methods of the invention minimize the cost of recovery. Because this treatment does not utilize ionizing radiation, it is repeatable.

BRIEF DESCRIPTION OF THE DRAWINGS

The foregoing and other objects, features and advantages of the invention will be apparent from the following description and from the accompanying drawings, in which like reference characters refer to the same parts throughout the different views. The drawings illustrate principles of the invention and, although not to scale, show relative dimensions.

DETAILED DESCRIPTION OF AN ILLUSTRATIVE EMBODIMENT OF THE INVENTION

Figure 1:
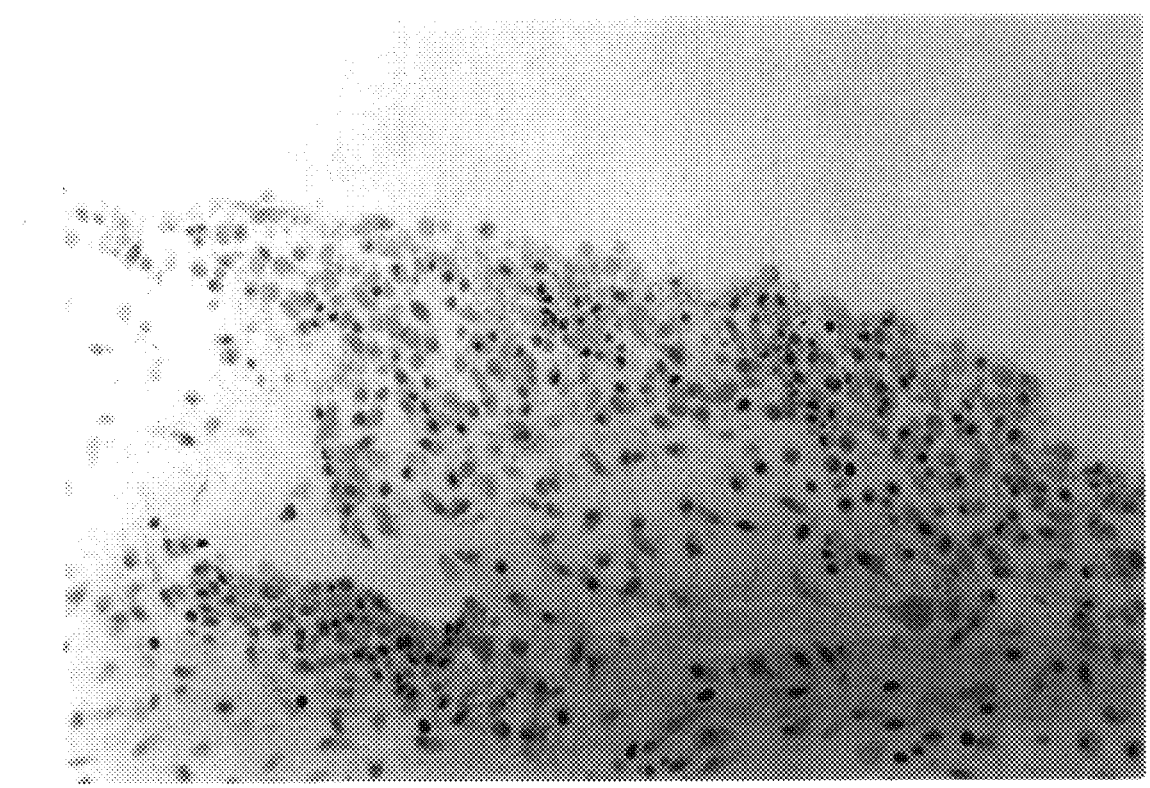
FIG. 1 is synovial tissue from an antigen-induced arthritis rabbit knee focusing on the hyperplastic synovial lining.
Figure 2:
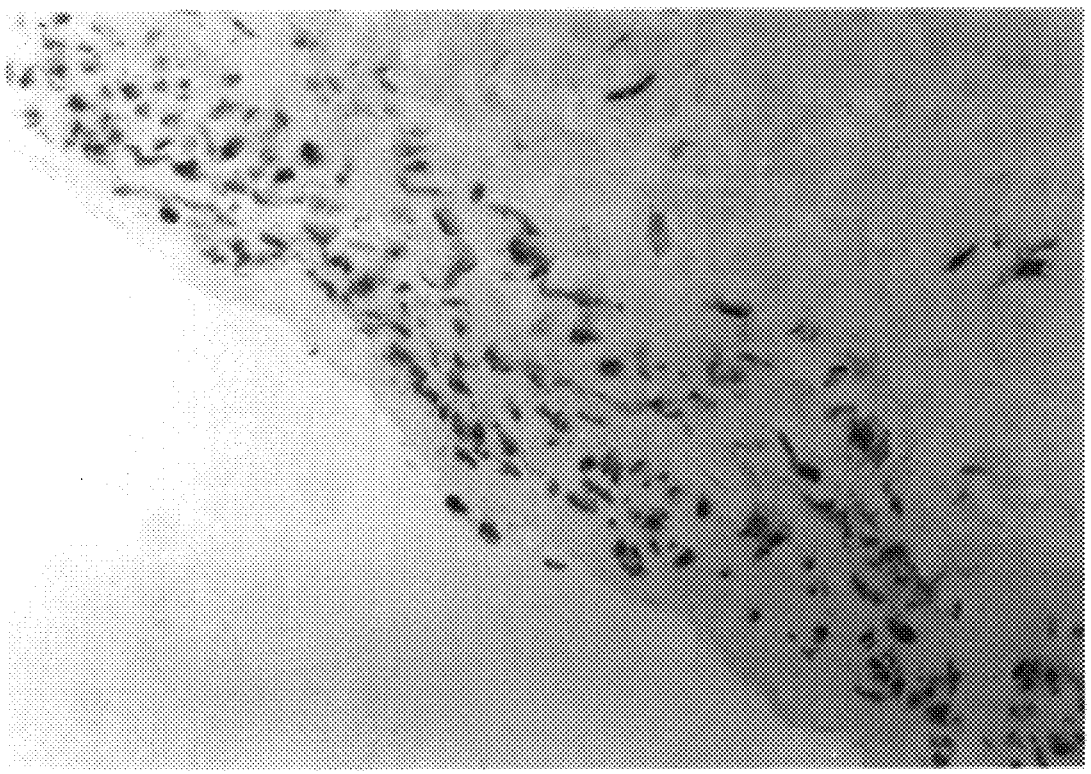
FIG. 2 is a focused ultrasound treated area from the same knee. The sonicated area is consistent with coagulation necrosis as the synovial cells display nuclear alterations and appear pyknotic.
Figure 3:
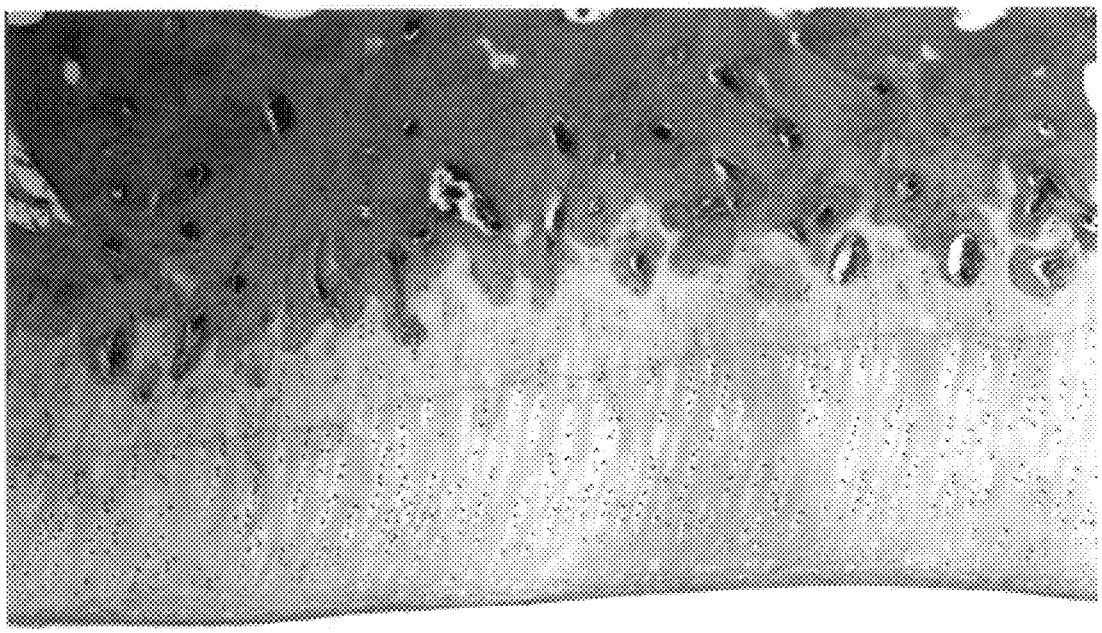
FIG. 3 is a femoral condylar cartilage and underlying bone appear unaffected by the ultrasound treatment of adjacent synovium. The variability in staining observed in the cartilage is a reflection of the proteoglycan depletion that occurs in the animal model.

The present invention is based in part on the discovery of a novel method for treating arthritis and other hyperplastic synovial joint diseases. Through the noninvasive introduction of ultrasound energy into the joint, the hyperplastic synovial membrane or pannus can be destroyed or modified to reduce the growth or inflammatory response and prevent or decrease the amount of joint deterioration and/or destruction.

In a preferred embodiment of the invention, a spherical transducer which provides the ultrasound energy is focused on the area of the pannus to be destroyed or modified. The ultrasound energy provided by the transducer is preferably delivered to the pannus with a frequency in the range of 1.0 to 10 MHz. This energy destroys or modifies the pannus so that inflammation of the joint is reduced and joint mobility and range of motion is increased.

According to one embodiment of the invention, the novel system may deliver ultrasonic energy in the range of about 0.2 to about 50 MHz. More particularly, a range of about 0.5 to about 20 MHz is preferred and still more preferable is a range of about 1.0 to about 10 MHz.

In another aspect, the invention provides a method for the treatment of arthritis and other inflammatory joint diseases, comprising the steps of focusing a beam of ultrasound energy on the pannus so that the internal temperature of the pannus causes coagulation of the pannus. Preferably, the coagulation of the pannus includes the destruction or reduction in size of the pannus caused by the transformation of the liquid component of the pannus.

In still another aspect, the invention provides a method for the treatment of arthritis and other hyperplastic synovial joint diseases, comprising the steps of focusing a beam of ultrasound energy on the pannus so that the cavitation effects of the ultrasound energy destroys or modifies the pannus. Preferably, the cavitation effects of the ultrasound energy destroys or reduces the size of the pannus by forming cavities within the pannus tissue.

In yet another aspect, the invention provides a method for the treatment of arthritis and other hyperplastic synovial joint diseases, comprising the steps of focusing multiple short and high powered bursts of ultrasound energy so that the pannus is vaporized. Preferably, delivery of these multiple high powered bursts of ultrasound energy create an internal temperature in the pannus of between 55 and 100° C. Still more preferably, the ultrasound energy vaporizes the liquid component of the pannus tissue thus destroying or reducing the size of the pannus.

In still yet another aspect, the invention provides a method for the treatment of arthritis and other hyperplastic synovial joint diseases, comprising the steps of utilizing a multiphase array to focus a beam of ultrasound energy on the pannus so that the pannus is destroyed or modified. Preferably, the ultrasound phased array is comprised of various components. The ultrasound phased array system generally comprises a control system, controlling a channel driving system, that provides power to a matched ultrasonic transducer. The channel driving system comprises a power generation system, and a phase regulation system. The control system provides a power set point input and a feedback enable signal to the power generation, and a phase set point input and feedback select signal to the phase regulation system. The power generation system provides an output driver signal to the matched transducer, and provides a power feedback signal input to itself. The phase regulation system includes a phase feedback signal from the power generation system output or alternatively the matched transducer, to provide phase correction to the power generation system.

In an additional aspect, the previously described methods utilize a lens to focus the beam of ultrasound energy. Preferably, the lens is an acoustic lens that can be translocated or rotated in space to focus the wave of ultrasound energy at a particular focal point.

In still yet another aspect, the previously described methods do not damage the surrounding normal tissue or bone. Preferably, the ultrasound energy delivered to the joint is precisely controlled so as to destroy or modify only the damaged or inflamed or hyperplastic tissues and do not affect the surrounding areas of tissue or bone near the inflamed area to be treated which is not also diseased.

EXAMPLES

EXAMPLE 1

Treatment of Pannus in Joints in Rabbits

Pannus was created in the knees of rabbits was caused by injection of ovalbumin into knee joints three weeks following an initial sensitization of the animals. The sensitization was performed by intradermal injection of a mixture of Freund's complete adjuvant and/or albumin on two occasions separated by three weeks. The pannus was allowed to progress for two weeks prior to the therapy. Using MRI as an image guidance system, focused ultrasound beam was delivered to the pannus of the inflicted joints at 60 W (RF) for a duration of 10 second in order to cover the target volume. The sonications were repeated in different locations of the pannus. Tissue temperature was monitored by MRI. This temperature was sufficient to induce coagulation of the pannus.

After ultrasound treatment, the animals were sacrificed and their tissues harvested and analyzed. Histologic evaluation of the tissue samples of the treated rabbits showed that the pannus had completely necrosed. Furthermore, no damage to the surrounding normal tissue or bone of the joints was evident.

It is thus seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

We claim:

1. A method for destroying the pannus in a joint of a subject, comprising the steps of:
   providing a transducer which produces a beam of ultrasound energy;
   delivering said beam of ultrasound energy;
   directing said beam of ultrasound energy on the pannus;
   utilizing a multiphase array to focus a beam of ultrasound energy on the pannus; and
   maintaining said beam on the pannus wherein the energy of said beam destroys the pannus.

2. The method of claim 1, further comprising the step of using a lens to focus the beam of ultrasound energy.

3. The method of claim 1, further comprising the step of using MRI, CT, or ultrasound as an image guidance system.

4. The method of claim 3, further comprising the step of controlling the image guidance system with a central processing unit for precise guidance.

5. The method of claim 1, further comprising the step of selectively destroying only the pannus.

6. The method of claim 1, further comprising the step of delivering said beam of ultrasound energy in the range of about 0.2 to about 50 MHz.

7. The method of claim 1, further comprising the step of delivering said beam of ultrasound energy in the range of about 0.5 to about 20 MHz.

8. The method of claim 1, further comprising the step of delivering said beam of ultrasound energy in the range of about 1.0 to about 10 MHz.

9. A method for destroying the pannus in a joint of a subject, comprising the steps of:
- providing a transducer which produces a beam of ultrasound energy;
- delivering said beam of ultrasound energy;
- directing said beam of ultrasound energy on the pannus wherein the energy of said beam raises the internal temperature of the pannus;
- utilizing a multiphase array to focus a beam of ultrasound energy on the pannus; and
- maintaining said beam on the pannus wherein the internal temperature of the pannus is elevated to a level which is sufficient to destroy the pannus by coagulating the pannus.

10. A method for destroying the pannus in a joint of a subject, comprising the steps of:
- providing a transducer which produces a beam of ultrasound energy;
- delivering said beam of ultrasound energy;
- directing said beam of ultrasound energy on the pannus wherein gas bubbles form within the pannus;
- utilizing a multiphase array to focus a beam of ultrasound energy on the pannus; and
- maintaining said beam on the pannus wherein the gas bubbles destroy the pannus.

11. A method for destroying the pannus in a joint of a subject, comprising the steps of:
- providing a transducer which produces a beam of ultrasound energy;
- delivering said beam of ultrasound energy;
- directing said beam of ultrasound energy on the pannus wherein said beam of ultrasound energy raises the internal temperature of the pannus;
- utilizing a multiphase array to focus a beam of ultrasound energy on the pannus; and
- maintaining said beam on the pannus wherein the internal temperature of the pannus is sufficient to destroy the pannus by vaporization.

12. A method of treating arthritis by destroying the pannus in a joint of a subject, comprising the steps of:
- providing a transducer which produces a beam of ultrasound energy;
- delivering said beam of ultrasound energy;
- directing said beam of ultrasound energy on the pannus;
- utilizing a multiphase array to focus a beam of ultrasound energy on the pannus; and
- maintaining said beam on the pannus wherein the energy of said beam destroys the pannus.

* * * * *

UNITED STATES PATENT AND TRADEMARK OFFICE
CERTIFICATE OF CORRECTION

PATENT NO. : 6,074,352
DATED : June 13, 2000
INVENTOR(S) : Hynynen et al.

It is certified that error appears in the above-identified patent and that said Letters Patent is hereby corrected as shown below:

On Cover page : under Attorney, Agent, or Firm, delete "Giulio A. Conti, Jr., Esq." and insert --Giulio A. DeConti, Jr., Esq.--

Signed and Sealed this

First Day of May, 2001

*Attest:*

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,074,352 | Page 1 of 1 |
| APPLICATION NO. | : 09/048866 | |
| DATED | : June 13, 2000 | |
| INVENTOR(S) | : Kullervo Hynynen et al. | |

It is certified that error appears in the above-identified patent and that said Letters Patent is hereby corrected as shown below:

At Column 1, line 5 of the printed patent, please insert the following Statement Regarding Federally Sponsored Research or Development:

--This invention was made with Government support under Grant No. CA046627 awarded by the National Institutes of Health. The Government has certain rights in this invention.--

Signed and Sealed this

Seventh Day of July, 2009

JOHN DOLL
*Acting Director of the United States Patent and Trademark Office*